(12) United States Patent
Nowak et al.

(10) Patent No.: US 9,872,675 B2
(45) Date of Patent: Jan. 23, 2018

(54) SURGICAL RETRACTOR WITH ANGLING DEVICE

(71) Applicant: Thompson Surgical Instruments, Inc., Traverse City, MI (US)

(72) Inventors: Steve Nowak, Traverse City, MI (US); Christopher T. Martin, Empire, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 655 days.

(21) Appl. No.: 14/558,284

(22) Filed: Dec. 2, 2014

(65) Prior Publication Data

US 2015/0182211 A1 Jul. 2, 2015

Related U.S. Application Data

(60) Provisional application No. 61/910,846, filed on Dec. 2, 2013.

(51) Int. Cl.
*A61B 17/02* (2006.01)
*A61B 17/29* (2006.01)

(52) U.S. Cl.
CPC .. *A61B 17/0206* (2013.01); *A61B 2017/2927* (2013.01)

(58) Field of Classification Search
CPC .................................................. A61B 17/0206
USPC ................................................ 600/231, 229
See application file for complete search history.

(56) References Cited

U.S. PATENT DOCUMENTS

| | | | | |
|---|---|---|---|---|
| 5,944,736 A | * | 8/1999 | Taylor | A61B 17/0206 600/201 |
| 5,976,171 A | * | 11/1999 | Taylor | A61B 17/0206 600/201 |
| 6,074,343 A | * | 6/2000 | Nathanson | A61B 17/0206 600/214 |
| 6,315,718 B1 | * | 11/2001 | Sharratt | A61B 17/02 600/228 |
| 6,368,271 B1 | * | 4/2002 | Sharratt | A61B 17/025 600/228 |
| 6,997,872 B1 | * | 2/2006 | Bohanan | A61B 17/02 600/210 |
| 8,727,975 B1 | * | 5/2014 | Pfabe | A61B 17/0206 600/231 |
| 9,592,041 B2 | * | 3/2017 | DeRidder | A61B 17/0206 |
| 9,649,101 B2 | * | 5/2017 | Karpowicz | A61B 17/0293 |
| 2005/0215866 A1 | * | 9/2005 | Kim | A61B 17/0293 600/233 |

(Continued)

*Primary Examiner* — David Bates
(74) *Attorney, Agent, or Firm* — McAndrews, Held & Malloy, Ltd.

(57) ABSTRACT

A physical retractor apparatus and method for retracting anatomy during surgery wherein the apparatus includes a handle rod, a body portion, a retractor blade and a mechanism which allows the retractor blade to be angularly adjusted, and secured, to one of any number of angular positions. The retractor blade may be first manually positioned to a gross angular position and thereafter fine tuned in angular position. The adjustment mechanism includes a pair of arms forced together to contract about a pivot pin to set an angular position and a threaded screw device which is rotatable to adjust further the angular position.

12 Claims, 8 Drawing Sheets

(56) References Cited

U.S. PATENT DOCUMENTS

| | | | |
|---|---|---|---|
| 2007/0038033 A1* | 2/2007 | Jones | A61B 17/02 600/219 |
| 2008/0021285 A1* | 1/2008 | Drzyzga | A61B 1/32 600/215 |
| 2008/0114209 A1* | 5/2008 | Cohen | A61B 17/0206 600/210 |
| 2008/0183046 A1* | 7/2008 | Boucher | A61B 17/0206 600/232 |
| 2008/0188718 A1* | 8/2008 | Spitler | A61B 17/0206 600/213 |
| 2009/0105547 A1* | 4/2009 | Vayser | A61B 17/0206 600/228 |
| 2010/0217089 A1* | 8/2010 | Farley | A61B 17/02 600/213 |
| 2010/0256454 A1* | 10/2010 | Farley | A61B 17/02 600/210 |
| 2012/0245431 A1* | 9/2012 | Baudouin | A61B 17/0206 600/213 |
| 2013/0046147 A1* | 2/2013 | Nichter | A61B 1/32 600/228 |

* cited by examiner

SURGICAL RETRACTOR WITH ANGLING DEVICE

RELATED APPLICATIONS

This application claims priority to, and is a Non-Provisional of, U.S. Provisional Application No. 61/910,846, having a filing date of Dec. 2, 2013, which is incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention relates to a surgical apparatus for retracting anatomy to provide exposure of an operative surgical site and, more particularly, to a retraction apparatus in which a retractor blade is angularly-adjustable.

In surgical operations, it is customary to use a retraction device in order to properly access internal organs and bone structures. Such devices are particularly designed to hold back the anatomy in the immediate area of the operative site to enable a surgeon to have both an optimal view of the site and a sufficiently-open area within which to work.

Known retraction systems typically include a frame assembly mounted to an operating table, a plurality of support rods extending from such frame, a retractor device having a blade and handle, and a variety of clamping devices for use in securing the support rods to the frame and the retractor devices to the support rods. The majority of the above-described retractor system is located above the operative site where surgery is to be performed—the retractor blade itself being the only component in substantial contact with the retracted anatomy.

The usefulness of any retractor device is necessarily limited by the number of ways that the retractor can be positioned with respect to the retracted anatomy as well as the ease with which the surgeon can adjust the relative position of the retractor both before and during surgery. Obviously, the less obstructive and more versatile a retractor device is, the more desirable it becomes for use in the above-described manner.

Given the variances in patient size as well as the types of surgery with which retractor systems are used, a variety of adjustment mechanisms have been developed in this field of art. One such mechanism is described in Applicant's U.S. Pat. No. 5,902,233 in which the retractor blade may be angularly adjustable. However, such a mechanism is confined to a single type of adjustment and does not allow for a quick gross angle positioning of the blade followed by a fine tuning of the angular position of the blade.

It is therefore an object of the present invention to provide a novel surgical retractor apparatus having a retractor blade which is angularly adjustable with respect to its handle.

It is a second object of the present invention to provide an angling surgical retractor apparatus whereby the angular position of the retractor blade may be adjusted after the handle of the apparatus is secured to a support rod of other support apparatus.

It is another object of the present invention to provide an angling surgical retractor apparatus whereby the retractor blade may be fine tuned from its present angular position.

It is a further object of the present invention to provide an angling surgical retractor apparatus whereby the retractor blade may be grossly adjusted in angle, and thereafter finely adjusted.

BRIEF SUMMARY OF THE INVENTION

Those and other objects of the present invention are achieved in a surgical retraction apparatus which retracts anatomy during all types of surgery. The apparatus is particularly applicable to those delicate procedures wherein it is desirable to have maximum exposure deep in the wound through a micro-incision. The device includes a handle rod which is intended to be fastened to a frame structure of a surgical operating table via some form of clamping device. At an end of the handle rod opposite that which is clamped, the device includes a pivoting head member to which one of any number of interchangeable retractor blades is connected. Mounted on the handle rod is structure which positions the head member and associated retractor blade in one of any number of angular positions.

In accordance with the preferred embodiment of the present invention, an adjustment clamp is first tightenable by the user to grossly adjust the angular position of the retractor blade and thereafter to finely adjust the angular position, so as to retract the anatomy exactly as the surgeon desires.

DETAILED DESCRIPTION OF THE INVENTION

Figure 1:
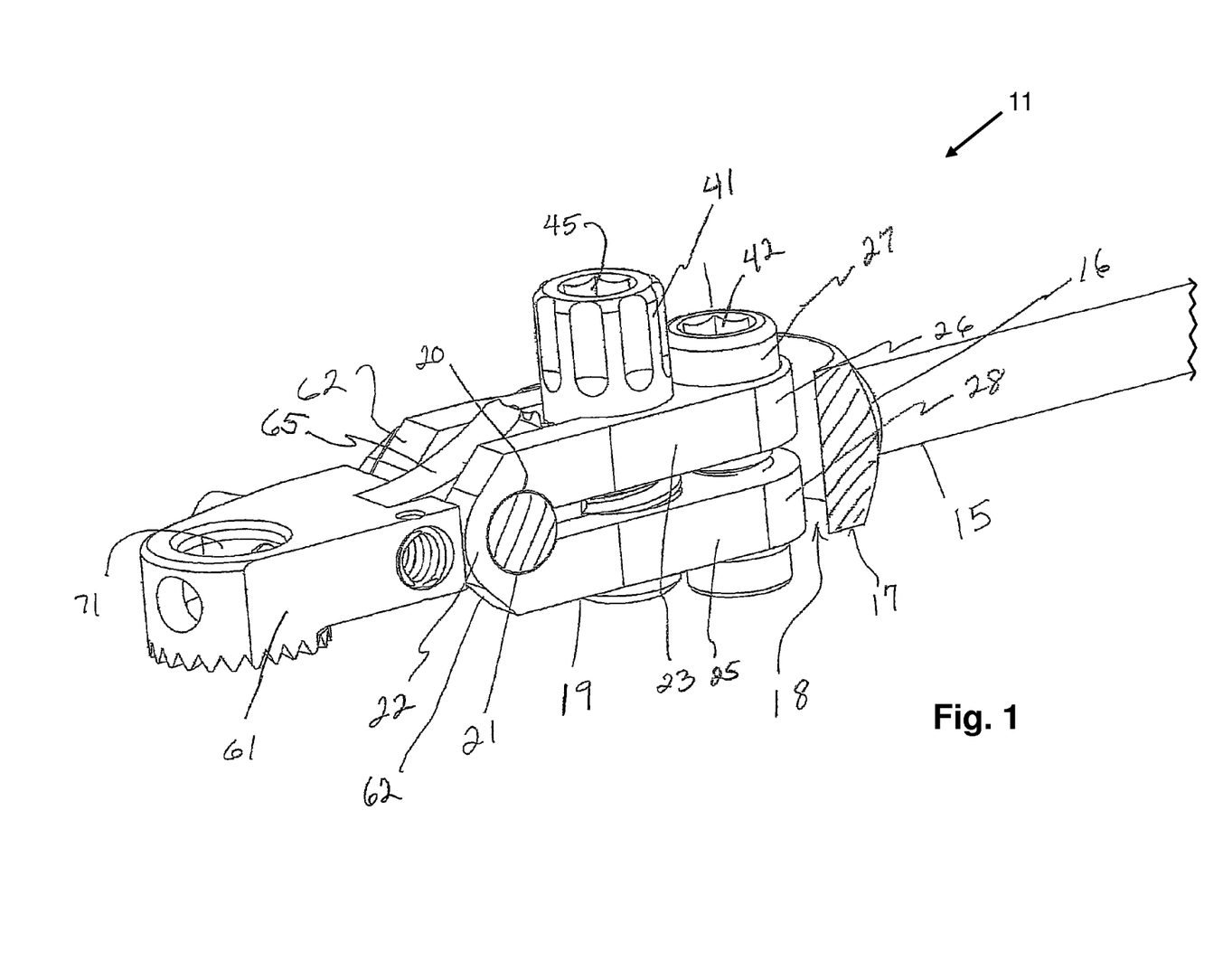
FIG. 1 is a perspective view of an embodiment of retractor apparatus according to the present invention.
Figure 2:
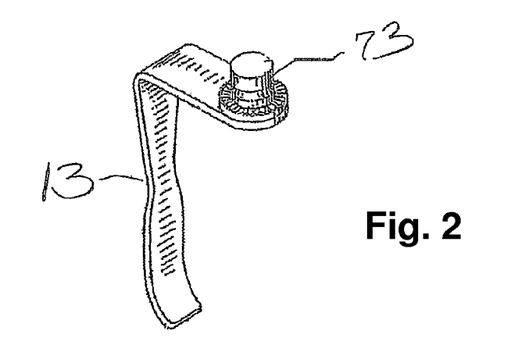
FIG. 2 is a perspective view of a retractor blade for connection to the retractor apparatus of FIG. 1.

Referring to FIG. 1, a surgical retractor 11 is shown. Retractor 11 includes a retractor blade 13, shown in FIG. 2. Typically, retractor 11 may be clamped to support rods (not shown) for location of blade 13 relative to an operative site. Retractor blade 13 is to be set in a desired angular position within the operative surgical site (not shown), as described below.

Should it be decided to change the angle with which retractor blade 13 engages the anatomy of the patient, the mounting of retractor apparatus 11 may be repositioned. U.S. Pat. No. 5,902,233 discloses a retractor apparatus in which the angle at which the retractor is set or established may be changed without repositioning of the retractor apparatus. This U.S. Pat. No. 5,902,233, is incorporated herein by reference.

Figure 4:
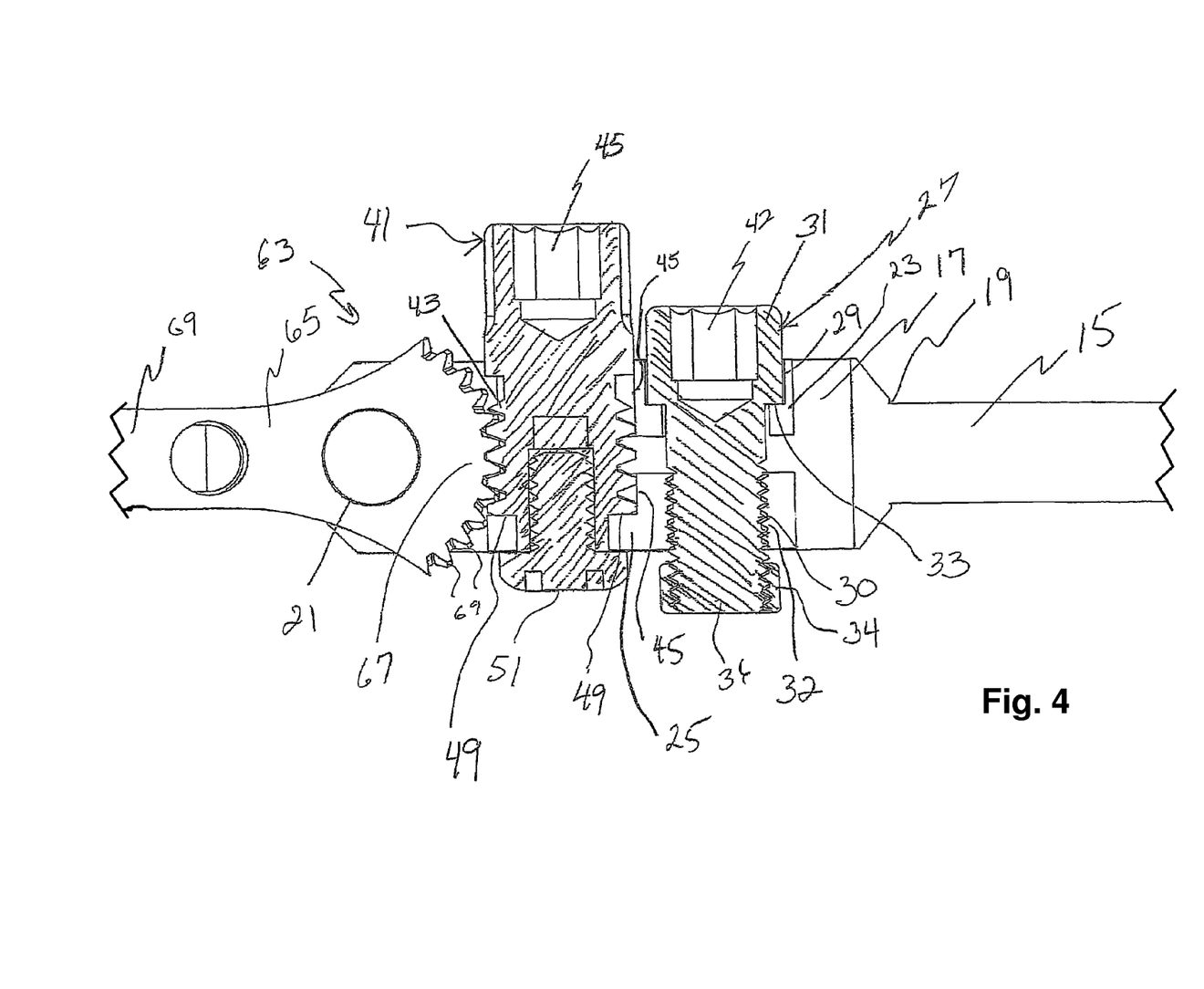
FIG. 4 is a cut away side view of a portion of the retractor apparatus of FIG. 1.

Referring again to FIG. 1, surgical retractor 11 includes a cylindrical mounting rod or handle 15 having a relative length as shown in FIG. 11. An integrally formed support member 17 is disposed at one end 16 of rod 15, as best seen in FIG. 4. FIG. 1 illustrates support member 17 having its left side removed for clarity of description.

Figure 6:
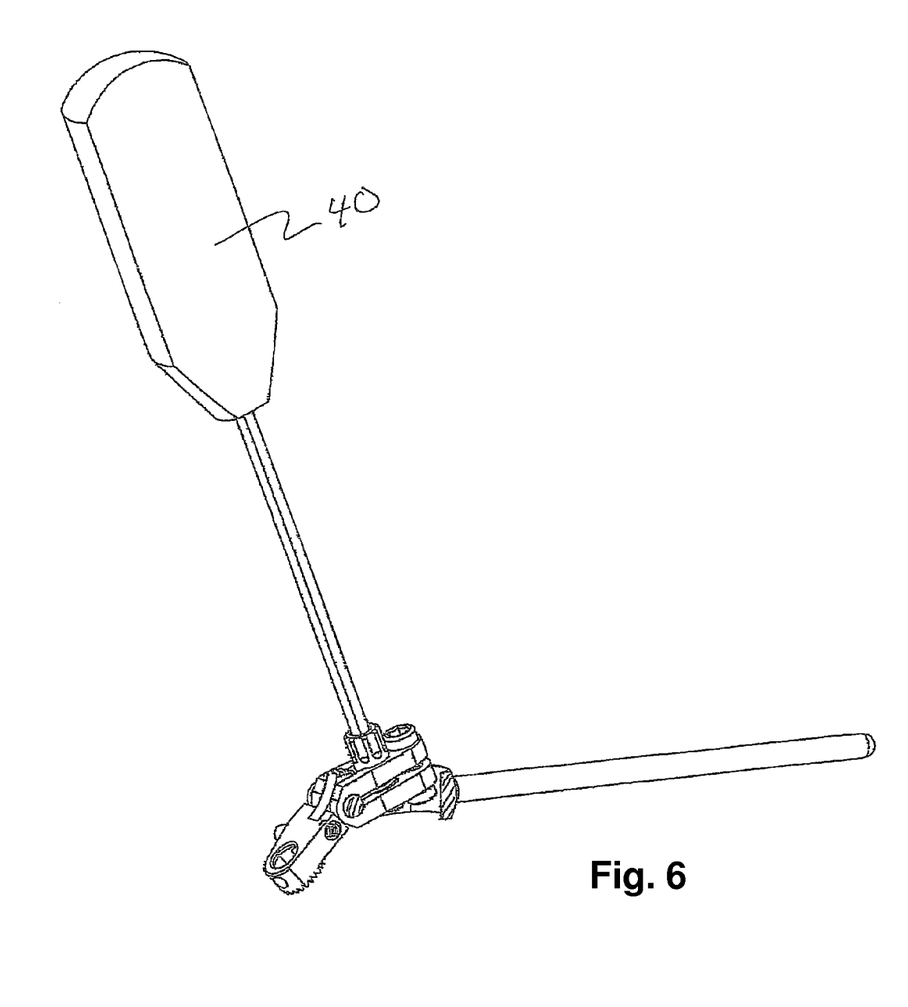
Figure 7:
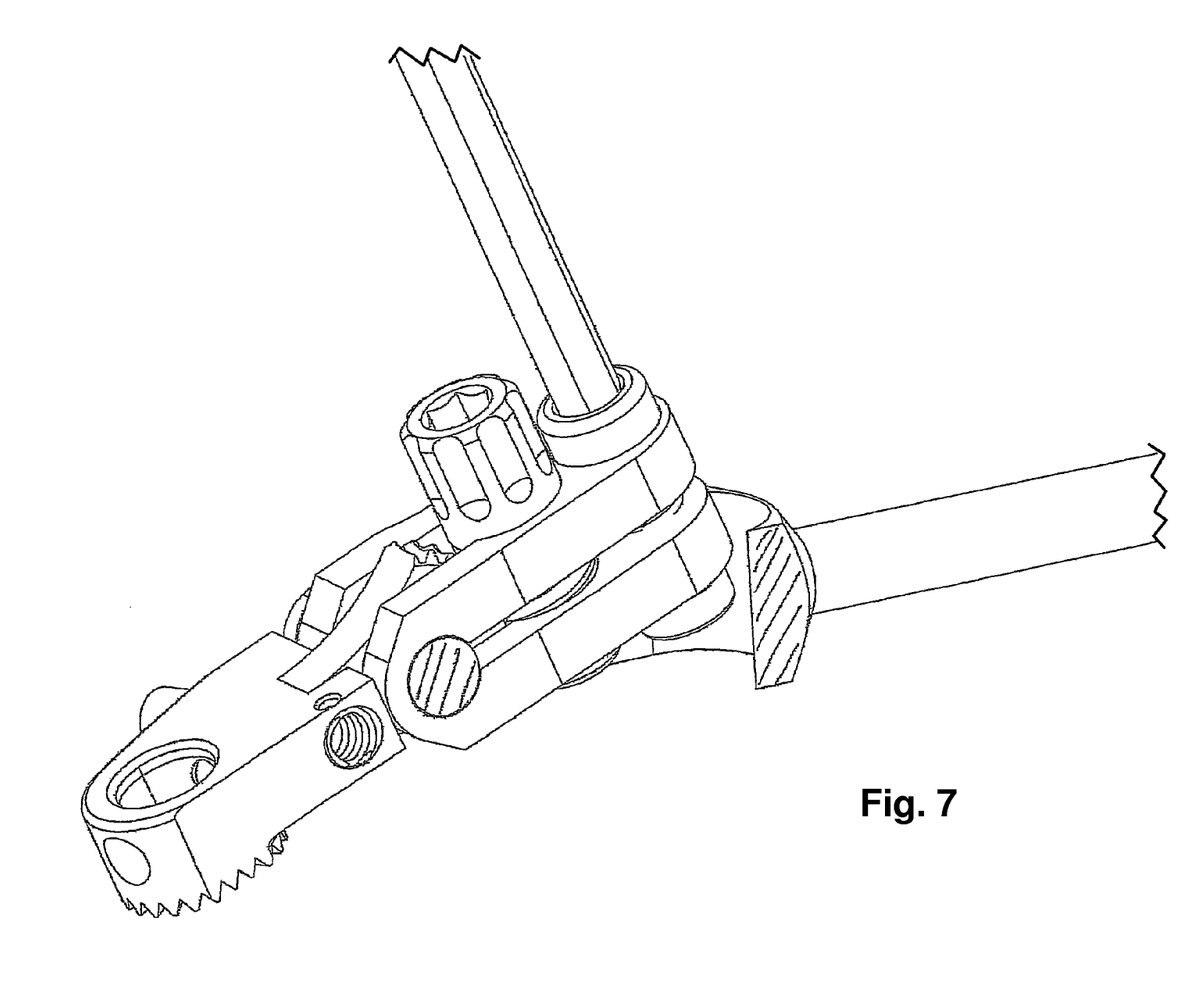
FIGS. 7 and 8 are each a perspective view of the retractor apparatus of FIG. 1 with the head of the retractor apparatus being located at different angular positions.
Figure 8:
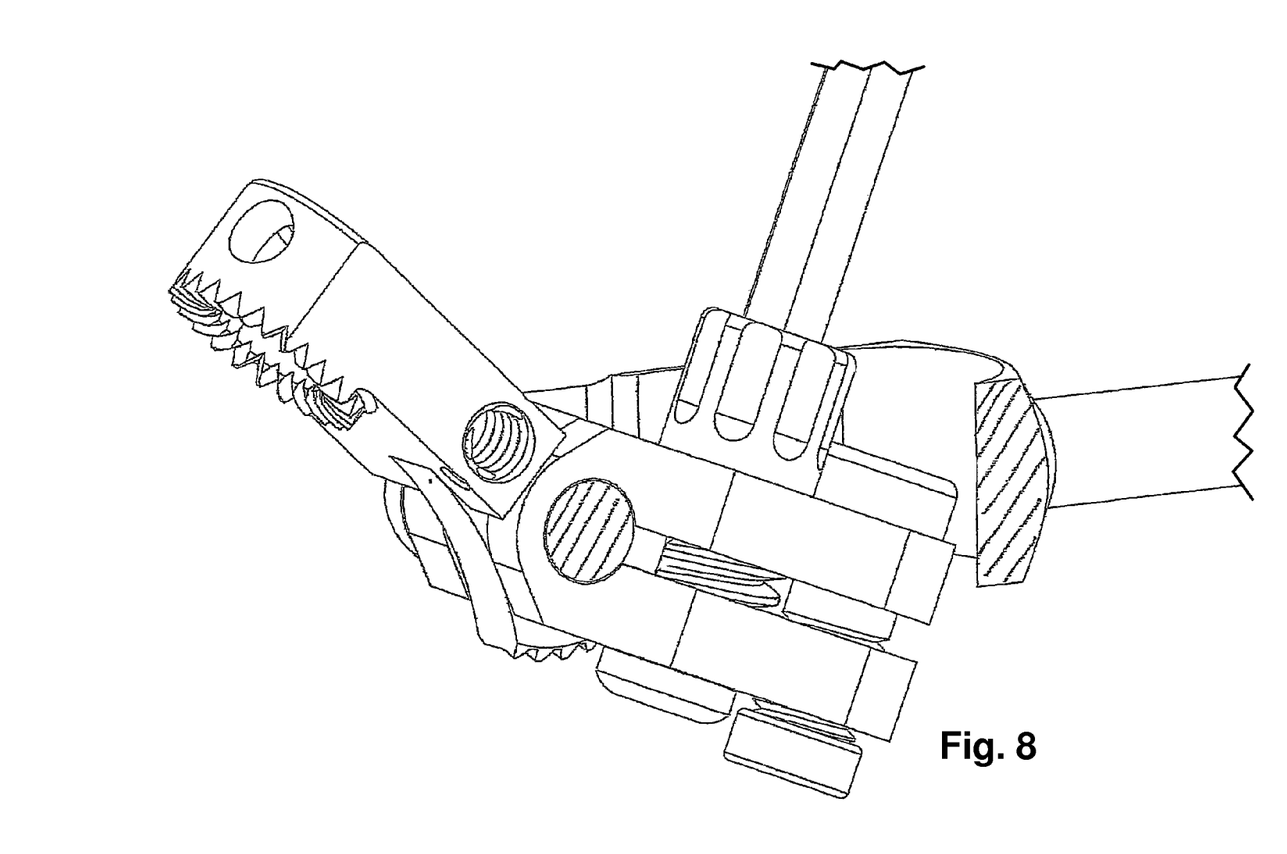

Support member 17 is generally U-shaped in configuration, having an open interior 18 for receiving a gross adjustment clamp 19 and a pivot pin 21. Pivot pin 21 is located to span across the interior space 18 at the distal end 22 of clamp 19. Gross adjustment clamp 19 is pivotally mounted to support member 17 via pivot pin 21, such that gross adjustment clamp 19 may pivot on pivot pin 21 relative to support member 17. FIGS. 6-8 illustrate the clamp in various pivot positions.

Referring again to FIG. 1, gross adjustment clamp 19 includes an upper clamp arm 23 and a lower clamp arm 25. The two clamp arms 23, 25 are forcibly moved together at their proximal ends 26, 28 by a control screw 27. The movement serves to clamp clamp 19 about pivot pin 21.

As shown in FIG. 4, control screw 27 includes threads 30 which mate with threads 32 formed in lower clamp arm 25. Control screw 27 is received in a cylindrical aperture 29 formed in the upper clamp arm 23 of gross adjustment clamp 19. As seen in FIG. 4, control screw 27 includes a head portion 31 which engages a stop portion 33 formed by aperture 29.

As control screw 27 is rotated clockwise, head portion 31 moves toward and engages stop portion 33 and forces the upper clamp arm towards the lower clamp arm. Control screw 27 is screwed into the lower clamp arm 25 engaging screw threads 32. An end cap 34 is screwed onto the bottom 36 of screw 27, for retaining screw 27 to clamp 19.

Referring again to FIG. 1, as the upper and lower clamp arms are forced towards one another, an aperture wall 20 formed in each clamp arm and which receives pivot pin 21 tightens or constricts around pivot pin 21 so as to secure clamp 19 at a rotational position onto pivot pin 21.

Figure 5:
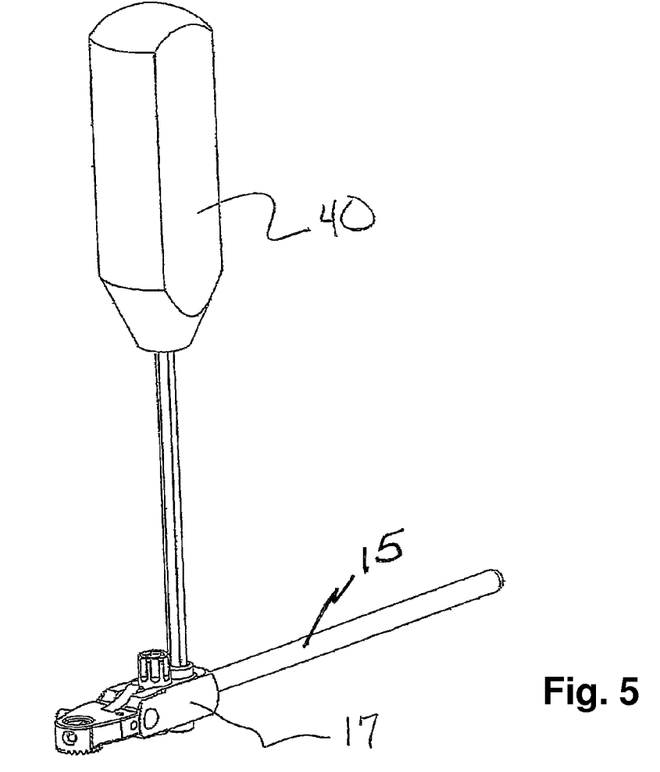
FIGS. 5 and 6 are each a perspective view of the surgical apparatus of FIG. 1 showing an adjustment device connected thereto and showing the head of the retractor apparatus being located at different angular positions.

Thus, the user initially untightens control screw 27 to permit manual rotation of clamp 19 about pivot pin 21. The user next manually positions clamp 19 at an angular position onto pivot pin 21 by manually rotating clamp 19 relative to pivot pin 21. After clamp 19 has been manually rotated to a particular angular position, for example as shown in FIG. 7, control screw 27 is tightened to secure clamp 19 in that particular angular position relative to pivot pin 21. As shown in FIG. 5, a screwdriver 40 is manually inserted into a screw driver receiving chamber 42 at the top portion of control screw 27 and rotated so as to rotate control screw 27.

Referring again to FIG. 1, a second control screw 41 serves to provide fine-tuned angling adjustments. Second control screw 41 is rotatable relative to gross adjustment clamp 19. As shown in FIG. 4, second control screw 41 includes (1) threads 43 on the exterior surface of screw 41 and (2) a screwdriver receiving chamber 45 at its upper end. Upper clamp arm 23 and lower clamp arm 25 include a screw-receiving wall 45 defining a cylindrical aperture as best seen in FIG. 4. Lower clamp arm 25 includes a receiving surface 49 against which second control screw 41 rotates.

Once second control screw 41 is positioned within the cylindrical aperture defined by wall 45, a screw 51 is driven up into the lower portion of second control screw 41 in order to hold the second control screw 41 onto the support member 17. Second control screw 41 is thus rotatably mounted to clamp 19.

Referring to FIG. 1, a head 61 extends outwardly distally from clamp 19 and is rotatably mounted onto pivot pin 21. Thus head 61 is movable relative to clamp 19. The outer end 22 of the clamp 19 is configured with beveled surfaces 62 to allow head 61 to rotate relative to pin 21. The rotation of head 61 about pin 21 is provided by action of second control screw 41. Control screw 41 engages a worm screw mechanism generally indicated at 63 in FIG. 4.

As shown in FIG. 4, worm screw mechanism 63 includes a gear arm 65 having an arcuate shaped proximal end 67 which carries gear teeth 69. Gear teeth 69 intermesh with threads 43 carried by second control screw 41. As the second control screw 41 is rotated, gear teeth 69 are moved causing arm 65 to rotate about pivot pin 21. As shown in FIG. 6, screwdriver 40 is manually inserted into the top portion chamber 45 (FIG. 1) of control screw 41 and rotated so as to rotate control screw 41.

Figure 3:
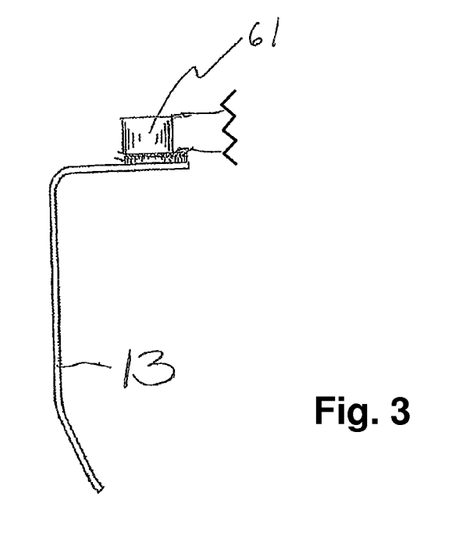
FIG. 3 is a side view of the retractor blade of FIG. 2 shown connected to an area of the retractor apparatus of FIG. 1.

The distal end 69 (FIG. 4) of gear arm 65 is secured to head 61, as shown in FIG. 1. The head 61 includes an aperture 71 (FIG. 1) for receiving a nipple 73 (FIG. 2) of retractor blade 13, as shown being received in FIG. 3. This connection of the blade 13 to head 61 may be done in a variety of ways including that described in U.S. Pat. No. 5,902,233 and described in U.S. Pat. No. 8,360,971, both patents are herein incorporated by reference.

Figure 9:
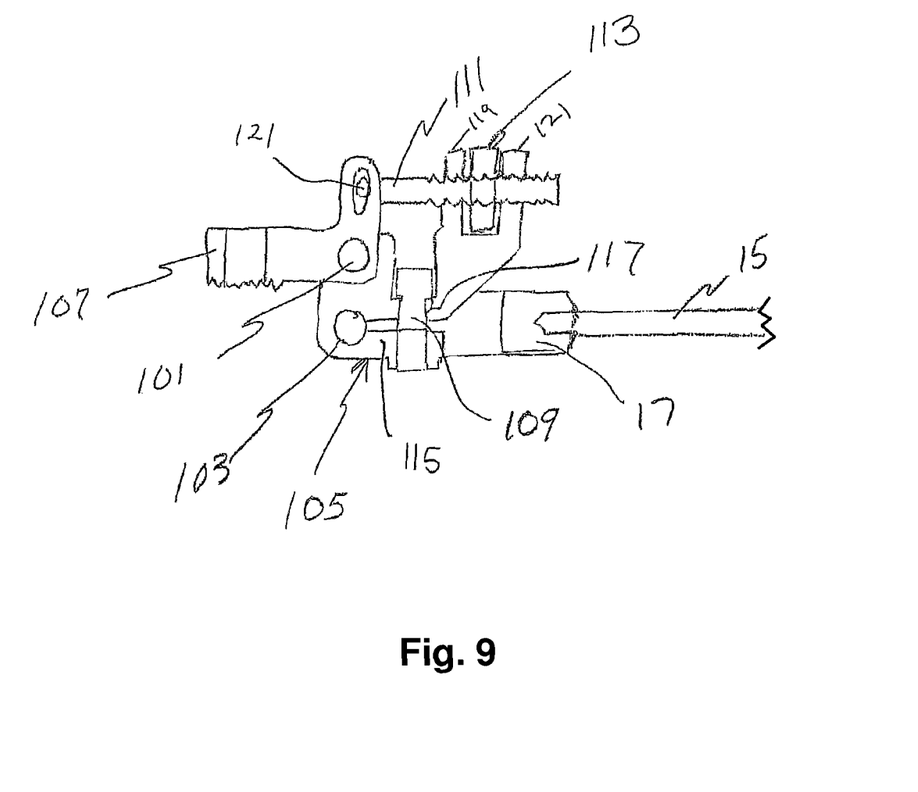
FIG. 9 is a side view of a second embodiment of retractor apparatus according to the present invention.

Referring to FIG. 9, a second embodiment is shown, in which two pivot pins 101, 103 provide separate axes of pivoting. The axes are vertically aligned. A clamp 105 (corresponding to gross adjustment clamp 19 of FIG. 1) includes two clamp arms 115, 117. Clamp 105 pivots on pivot pin 103 to adjust a first angle for the retractor blade (not shown) which is attached to a head 107 (corresponding to head 61 of FIG. 1). Clamp 105 is secured into a position onto pivot pin 103 by tightening of a screw 109 which pulls two clamp arms 115, 117 together. Pivot pin 103 is disposed in the support member 17, similar to pivot pin 21 of FIG. 1.

Head 107 is positioned on pivot pin 101 to provide further angular adjustment to head 107 after clamp 105 has been set at an angle on pivot pin 103. A screw 111 is rotated relative to a screw nut 113 in order to cause head 107 to pivot about the axis of pivot pin 101. Pivot pin 101 is secured to head 107. As shown, arm 117 includes a pair of arms 119, 121 for receiving a screw nut 113, and arm 117 includes a pair of apertures through which screw 111 passes. The distal end of the screw 111 engages an aperture 121 formed in head 107 for forward and for backward movement of head 107 about the axis of pivot pin 101 as the screw 111 is rotated.

While the present technology has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed.

The invention claimed is:

1. A surgical retractor comprising:
   an arm having a distal end;
   a support member formed integral to said arm at said distal end;
   a pivot pin secured to said support member and defining an axis;
   a blade having an attachment member;

a head having an opening at one end and configured at said one end to receive the attachment member, said head having an opening at another end and configured at the another end to receive said pivot pin allowing rotation of said head about said axis, said another end having gear teeth;

a gross adjustment clamp rotatably mounted about said axis, said gross adjustment clamp including a pin receiving aperture for receiving said pivot pin, said gross adjustment clamp operable to frictionally tighten itself against said pin to secure itself at a rotational position relative to said pivot pin, said gross adjustment clamp including:

(1) a first control screw rotatably mounted to said adjustment clamp, and being rotatable for controlling the configuration of said pin receiving aperture to frictionally tighten said gross adjustment clamp against said pivot pin; and (2) a second control screw rotatably mounted to said adjustment clamp and having screw threads engaging said gear teeth of said head, said second control screw for controlling rotation of said head about said pivot axis.

2. The surgical retractor of claim 1 wherein said blade is detachably mounted to said head so as to permit removal of the blade relative to said head.

3. The surgical retractor according to claim 1, wherein said arm is cylindrical in shape.

4. The surgical retractor according to claim 1, wherein said support member is U-shaped in configuration.

5. The surgical retractor according to claim 1, wherein said pivot pin is cylindrical.

6. The surgical retractor according to claim 1, wherein said head rotates on said pivot pin, and said another end of said head carries said gear teeth, and wherein said gear teeth are disposed to project into said gross adjustment clamp and mate with said screw threads of said second control screw.

7. The surgical retractor according to claim 1, wherein said gross adjustment clamp is formed of two planar members connected together at a first end, said two planar members include an aperture having cylindrically shaped walls for receiving said pin, said aperture being restricted by movement of said two planar members toward each other by action of rotation of said first control screw.

8. The surgical retractor according to claim 1, wherein said first control screw is located at the proximal end of said gross adjustment clamp.

9. The surgical retractor according to claim 1, wherein said second control screw is located between said pivot pin and said first central screw.

10. The surgical retractor according to claim 1, wherein said gross adjustment clamp is manually pivotable about said axis.

11. The surgical retractor according to claim 1, wherein said first and second control screws each include a screw head shaped to receive a hexagon screwdriver for manual movement of said first control screw and said second control screw.

12. A surgical retractor comprising:

an arm having a distal end;

a support member formed integral to said arm at said distal end;

a first pivot pin secured to said support member and defining a first axis;

a blade having an attachment member;

a head having an opening at one end and configured at said one end to receive the attachment member;

a gross adjustment clamp rotatably mounted about said first axis, said gross adjustment clamp including a pin receiving aperture for receiving said first pivot pin, said gross adjustment clamp operable to frictionally tighten itself against said first pin to secure itself at a rotational position relative to said first pivot pin, said gross adjustment clamp including:

(1) a second pivot pin defining a second axis; and wherein said head having an opening at another end and configured at the another end to receive said second pivot pin allowing rotation of said head about said second axis;

(2) a first control screw rotatably mounted to said adjustment clamp, and being rotatable for controlling the configuration of said pin receiving aperture to frictionally tighten said gross adjustment clamp against said first pivot pin; and (3) a second control screw rotatably mounted to said adjustment clamp, said second control screw for controlling rotation of said head about said second pivot axis.

* * * * *